(12) United States Patent
Joly et al.

(10) Patent No.: US 6,429,345 B1
(45) Date of Patent: Aug. 6, 2002

US006429345B1

(54) PROCESS FOR PRODUCTION PHENYLALKANES USING A CATALYST BASED ON A ZEOLITE WITH STRUCTURE TYPE EUO

(75) Inventors: Jean-François Joly, Lyons; Fabio Alario, Neuilly sur Seine; Elisabeth Merlen, Rueil-Malmaison; Julia Magne-Drisch, Vilette de Vienne, all of (FR)

(73) Assignee: Institut Francais du Petrole (FR)

( * ) Notice: Subject to any disclaimer, the term of this patent is extended or adjusted under 35 U.S.C. 154(b) by 0 days.

(21) Appl. No.: 09/598,460

(22) Filed: Jun. 22, 2000

(30) Foreign Application Priority Data

Jun. 22, 1999 (FR) ............................................. 99 07969

(51) Int. Cl.$^7$ ................................................. C07C 2/66
(52) U.S. Cl. ........................ 585/467; 585/446; 585/455; 585/323
(58) Field of Search ................................ 585/446, 455, 585/467, 323

(56) References Cited

U.S. PATENT DOCUMENTS

| | | | | |
|---|---|---|---|---|
| 4,537,754 A | * | 8/1985 | Casci et al. .................. | 423/708 |
| 4,593,138 A | * | 6/1986 | Casci et al. .................. | 585/481 |
| 5,877,370 A | | 3/1999 | Gajda ......................... | 585/467 |
| 5,993,642 A | * | 11/1999 | Mohr et al. ................... | 208/46 |

FOREIGN PATENT DOCUMENTS

| | | |
|---|---|---|
| EP | 0 042 226 A1 | 12/1981 |
| EP | 0 051 318 A1 | 5/1982 |
| EP | 0 537 389 A1 | 4/1993 |

* cited by examiner

*Primary Examiner*—Walter D. Griffin
(74) *Attorney, Agent, or Firm*—Miilen, White, Zelano & Branigan, P.C.

(57) ABSTRACT

The invention concerns a process for producing at least one compound selected from 2-, 3-, 4-, 5- and 6-phenylalkanes by alkylating benzene using at least one olefin containing at least 9 carbon atoms per molecule, in the presence of a catalyst comprising at least one zeolite with structure type EUO, at least partially in its acid form and at least one matrix, said zeolite comprising silicon and at least one element T selected from the group formed by aluminium, iron, gallium and boron (preferably aluminium and boron), with an Si/T atomic ratio of more than 5; said process being carried out at a temperature in the range 30° C. to 400° C., a pressure in the range 0.1 to 10 MPa, with an hourly space velocity of 0.50 to 200 h$^{-1}$, and a benzene/olefins mole ratio in the range 1:1 to 50:1.

22 Claims, No Drawings

PROCESS FOR PRODUCTION PHENYLALKANES USING A CATALYST BASED ON A ZEOLITE WITH STRUCTURE TYPE EUO

FIELD OF THE INVENTION

The present invention relates to the field of processes for producing phenylalkanes by alkylating benzene using at least one olefin comprising at least 9 carbon atoms, or comprising at least 14 carbon atoms. More particularly, the hydrocarbon feed used comprises at least one olefin containing 9 to 16 carbon atoms or 10 to 14 carbon atoms or, for example, the hydrocarbon feed used comprises at least one olefin containing 14 to 20 carbon atoms, in the presence of at least one catalyst comprising a zeolite with structure type EUO.

PRIOR ART

The phenylalkanes obtained in accordance with the invention constitute compounds for formulating biodegradable detergents after sulphonation.

Currently, bases for biodegradable detergents mainly use linear alkylbenzenes. This type of compounds is being produced in increasing quantities. In addition to its detergent power, one of the principal desired properties for these compounds after the sulphonation step is biodegradability. To ensure maximum biodegradability, the alkyl group must be linear and long with the distance between the sulphonate group and the terminal carbon on the linear chain being a maximum. The most important benzene alkylation agents are constituted by linear C9–C16 olefins, preferably C10–C14.

The linear alkylbenzenes obtained by alkylating benzene using linear olefin(s) are currently prepared using two major processes. The first process uses hydrofluoric acid as an acidic catalyst during the benzene alkylation step. The second uses a Friedel-Crafts type catalyst, in particular based on $AlCl_3$. Those two processes lead to the formation of 2-, 3-, 4-, 5- and 6-phenylalkanes. The principal drawback of those processes is connected to environmental constraints. The first process based on the use of hydrofluoric acid causes severe safety problems and discharge re-treatment problems. The second process causes the conventional problem linked with Friedel-Crafts type catalysts, namely with the discharges; for that type of process, the effluents have to be neutralised by a basic solution at the reactor outlet. These various drawbacks are supplemented by difficulties linked with separation of the catalyst from the reaction products in both processes.

These various constraints explain the interest in developing a process for alkylating benzene using linear olefins in the presence of a solid catalyst.

The prior art is primarily based on the use of catalysts with geometrical selectivity properties and leading to improved selectivity for 2- and 3-phenylalkane. Such catalysts with geometrical selectivity properties are constituted by zeolites. Thus United States patent U.S. Pat. No. 4,301, 317 claims a series of zeolites, namely: cancrinite, gmelinite, mordenite, offretite and ZSM-12. In particular, such zeolites are characterized in that their pore opening is in the range from about 6 to about 7 Å in diameter (1 Å=$10^{-10}$ m).

A patent application filed by the Applicant and published with number FR-2 697 246 demonstrates that catalysts based on dealuminated Y zeolite can be used. Y zeolites with a pore opening of close to 7.4 Å do not fall within the scope of U.S. Pat. No. 4,301,317. Regarding the use of Y zeolites, European patent EP-A-0 160 144 claims the use of low crystallinity Y zeolites (crystallinity in the range 30% to 80%), and U.S. Pat. No. 5,036,033 claims the use of Y zeolites rich in ammonium cations.

SUMMARY OF THE INVENTION

The invention provides a process for producing at least one compound selected from 2-, 3-, 4-, 5- and 6-phenylalkanes by alkylating benzene using at least one olefin containing at least 9 carbon atoms per molecule, in the presence of a solid zeolitic catalyst, characterized in that the catalyst comprises a matrix and a zeolite with structure type EUO, said zeolite comprising silicon and at least one element T selected from the group formed by aluminium, iron, gallium and boron, with an overall Si/T atomic ratio of more than 5, characterized in that said alkylation is carried out at a pressure in the range 0.1 to 10 MPa, a temperature in the range 30° C. to 400° C., and with an hourly space velocity of 0.50 to 200 $h^{-1}$, and a benzene/olefin(s) mole ratio in the range 1:1 to 50:1. More particularly, the invention concerns alkylating benzene using a linear olefin for the production of linear phenylalkanes.

IMPORTANCE OF THE INVENTION

We have discovered that the use of catalysts comprising at least one zeolite with structure type EUO, at least partially in its acid form and at least one matrix, said zeolite comprising silicon and at least one element T selected from the group formed by aluminium, iron, gallium and boron (preferably aluminium and boron), with an Si/T atomic ratio of more than 5, on alkylating benzene with olefin(s) as defined above, exhibits catalytic performances which are better than those of the catalysts described in the prior art. These novel catalysts are simultaneously highly active, highly selective and highly resistant to deactivation.

DESCRIPTION OF THE INVENTION

In the present invention, in addition to at least one olefin as defined above, the hydrocarbon feed used to alkylate the benzene ring can contain one or more paraffins, one or more other aromatic compound(s), one or more polyolefinic compound(s) (for example diolefinic), one or more mono- and/or polyunsaturated non linear olefin(s). These cuts can also contain one or more alpha-olefins in highly variable quantities from a trace to very large quantities which may even be in the majority compared with said feed. The olefins can be linear or branched olefins.

The process of the present invention can produce, preferably simultaneously, at least one compound selected from 2-, 3-, 4-, 5- and 6-phenylalkanes. In the case where the feed comprises linear olefins,, the process of the invention can produce mainly linear phenylalkanes. In the case where the feed comprises branched olefins, the process of the invention can produce mainly branched phenylalkanes.

The catalyst used in the present invention comprises at least one zeolite with structure type EUO, for example EU-1 zeolite, at least partially in its acid form and at least one matrix (binder), said zeolite comprising silicon and at least one element T selected from the group formed by aluminium, iron, gallium and boron, preferably aluminium and boron, with an Si/T atomic ratio of more than 5. Further, this catalyst formed, for example into beads or extrudates, has good mechanical strength.

EU-1 zeolite with structure type EUO, which has already been described in the prior art, has a unidimensional microporous network with a pore diameter of 4.1×5.7 Å (1 Å=1 Angström=1×10$^{-10}$ m) ("Atlas of Zeolite Structure Types", W. M. Meier and D. H. Olson, 4th edition, 1996). Further, N. A. Briscoe et al. have disclosed in an article in the review Zeolites (1988, 8, 74) that these unidimensional channels have lateral pockets with a depth of 8.1 Å and a diameter of 6.8×5.8 Å. The mode of synthesis of EU-1 zeolite and its physico-chemical characteristics have been described in European patent EP-B1-0 042 226. U.S. Pat. No. 4,640,829 concerns ZSM-50-zeolite, which has the same EUO structure type as EU-1 zeolite according to the "Atlas of Zeolite Structure Types", W. M. Meier and D. H. Olson, 4th edition, 1996. Said patent has a different mode of synthesis of the ZSM-50 to that described in EP-B1-0 042 226 regarding EU-1 zeolite. EP-A1-0 051 318 deals with TPZ-3 zeolite which has the same EUO structure type as EU-1 zeolite according to "Atlas of Zeolite Structure Types", W. M. Meier and D. H. Olson, 4th edition, 1996, and describes its use as a catalyst containing the zeolite as it is or formed. In said document, an example of forming TPZ-3 zeolite is the preparation of pellets, obtained by pelletising a mechanical mixture of powdered zeolite and binder. The pellets comprise TPZ-3 zeolite, a binder and optionally at least one element selected from the group formed by iron, cobalt, nickel, copper, zinc, ruthenium, rhodium, palladium, rhenium, osmium, iridium and platinum in the form of the metal or the metal oxide.

Surprisingly, the Applicant has discovered that a formed catalyst comprising:

at least one zeolite with structure type EUO, for example EU-1 zeolite, at least partially and preferably practically completely in its acid form, containing silicon and at least one element T selected from the group formed by aluminium, iron, gallium and boron, preferably aluminium and boron, and such that the overall Si/T atomic ratio is more than 5;

at least one matrix (binder), for example alumina; has remarkable properties for the production of phenylalkanes by alkylating benzene with mono-olefins.

More particularly, the matrix (binder) consists of at least one element selected from the group formed by natural clays (such as kaolin or bentonite), synthetic clays, magnesia, aluminas, silicas, silica-aluminas, titanium oxide, boron oxide, zirconia, aluminium phosphates, titanium phosphates, zirconium phosphates, preferably selected from the group formed by aluminas and clays.

The zeolite with structure type EUO, for example EU-1 zeolite, comprised in the catalyst of the invention is at least partially, preferably practically completely, in its acid form, i.e., in the hydrogen form (H+), the sodium content preferably being such that the Na/T atomic ratio is less than 0.5, radical less than 0.1, more preferably less than 0.02.

In a preferred implementation of the invention, a catalyst comprising a zeolite with structure type EUO is used wherein the crystal size is less than 5 micrometres ($\mu$m), normally less than 0.5 $\mu$m and still more preferably less than 0.2 $\mu$m. These crystals or crystallites are normally arranged as aggregates with a grain size such that the value of Dv,90 is less than or equal to 500 $\mu$m, normally less than 400 $\mu$m, usually less than 200 $\mu$m and preferably less than 50 $\mu$m. The aggregate size is determined by laser diffraction granulometry. This measurement is made on the zeolite powder suspended in water. After an initial measurement, the suspension is subjected to ultrasound for thirty seconds then a new measurement is made. The ultrasound used is characterized by a power of 50 W and a frequency of 50 kHz. This procedure is repeated until the result no longer changes ±5%). The size distribution of the aggregates defined by volume is calculated from the light signals collected by the detectors and using the Fraunhofer theory. Dv,X is defined as the diameter of the equivalent sphere such that the size of X % by volume of aggregates is less than said diameter. These characteristics are obtained directly during synthesis of the zeolite and/or by any method enabling the aggregate size to be reduced, such as post-synthesis grinding or suitable mixing before forming.

More particularly, the catalyst used in the process of the invention contains:

1% to 95%, preferably 3% to 90%, limits included, more preferably 5% to 85% by weight of at least one zeolite with structure type EUO, for example EU-1 zeolite, at least partially in its acid form, comprising silicon and at least one element T selected from the group formed by aluminium, iron, gallium and boron, preferably aluminium and boron, with an Si/T atomic ratio of more than 5;

at least one matrix or binder, providing the complement to 100% of the catalyst.

Said catalyst preferably has a bed crush strength, determined using the Shell method (SMS 1471-74), of more than 0.5 MPa, characterizing its mechanical strength.

The catalyst used in the process of the invention can be prepared using any method which is known to the skilled person and in particular by those described in the prior art concerning catalysts containing at least one zeolite with structure type EUO and in particular EU-1, ZSM-50 and TPZ-3 zeolite.

The catalyst used in the process of the invention is prepared, for example, firstly by treating a zeolite with structure type EUO, for example EU-1 zeolite, as synthesised, using any method which is known to the skilled person, for example by calcining in a stream of dry air, to eliminate the organic template occluded in the micropores of the zeolite, then carrying out at least one ion exchange step, for example using at least one solution of $NH_4NO_3$ to eliminate at least a portion, preferably practically all of the alkaline cations present in the cationic position in the zeolite, in particular sodium.

The catalyst preparation is continued by mixing the matrix and zeolite prepared as above then forming. The catalyst of the invention is generally formed so that the catalyst is preferably in the form of extrudates or beads, depending on its use. The conditions for forming the zeolite, the choice of matrix, optional prior grinding of the zeolite, the peptising process, addition of pore-forming agents, mixing time, the extrusion pressure if the catalyst is formed into extrudates, the speed and duration of drying, are determined for each matrix in accordance with rules which are well known to the skilled person, to obtain a catalyst which is preferably in the form of extrudates or beads.

Catalyst preparation is generally followed by calcining, normally at a temperature in the range 250° C. to 600° C., limits included. preferably preceded by drying, for example oven drying, at a temperature generally in the range from ambient temperature to 250° C., limits included, preferably in the range 40° C to 200° C. limits included. Said drying step is preferably carried out as the temperature is raised to carry out said calcining.

Forming the zeolite with structure type EUO used in the process of the invention, for example EU-1 zeolite, can be carried out using the as synthesised zeolite, i.e., containing the organic template and the alkaline cations, generally sodium. In that case the step for calcining in dry air, which is aimed at eliminating the organic template, and the ion exchange step using at least one solution of $NH_4NO_3$ are carried out on the formed catalyst comprising the zeolite and the matrix.

In a preferred variation of the process of the invention, in a reaction zone, benzene is reacted with a feed comprising at least one olefin, for example a linear olefin, in contact with a catalyst comprising a zeolite with structure type EUO having the characteristics defined above (alkylation reaction) then the product obtained is fractionated to separately recover a first fraction comprising unconverted benzene, a second fraction comprising at least one olefin, for example a linear olefin initially present in the feed (unconverted), a third fraction comprising 2-, 3-, 4-, 5- and 6-phenylalkanes and a fourth fraction comprising at least one polyalkylbenzene (or polyalkylbenzene fraction), this then usually being recycled at least in part to said reaction zone where it reacts with benzene in contact with said catalyst, to be at least partially transalkylated (transalkylation reaction) and a mixture of 2-, 3-, 4-, 5- and 6-phenylalkanes is recovered.

This variation of the invention is thus characterized in that the alkylation and transalkylation reactions take place jointly in the same reaction zone (i.e.,) in the same reactor in the presence of the same catalyst. Preferably, at least a portion of the first fraction comprising unconverted benzene is recycled to the reaction zone. Similarly, at least a portion of the second fraction comprising at least one unconverted linear olefin is preferably recycled to said reaction zone.

The recycled portion of the fourth fraction the major portion of which generally contains at least one dialkylbenzene is preferably substantially free of heavy alkylaromatic compounds which can be eliminated by fractionation.

In a further variation of the invention, at least a portion of the fourth fraction containing a polyalkylbenzene, the major portion of which generally contains at least one dialkylbenzene and which is preferably substantially free of heavy alkylaromatic compounds which can be eliminated by fractionation, can be sent to a second reaction zone which is different from the benzene alkylation zone containing a catalyst with structure type EUO, said second reaction zone containing a transalkylation catalyst (for example a zeolite with structure type EUO or any other transalkylation catalyst which is known to the skilled person) and being maintained under conditions which allow the formation of monoalkylbenzene by reaction between this or these polyalkylbenzene (s) and benzene which is fresh or at least a portion of which originates from the first fraction obtained during fractionation of the effluent from the mixture leaving the benzene alkylation zone containing a catalyst based on a zeolite with structure type EUO.

The alkylation step of the process of the present invention can be carried out at a temperature in the range 30° C. to 400° C., at a pressure of 0.1 to 10 MPa, with a liquid hydrocarbon flow rate (hourly space velocity) of about 0.5 to 200 volumes per volume of catalyst per hour and with a benzene/olefin mole ratio in the range 1:1 to 50:1.

In the implementation of the process of the invention which comprises a second distinct transalkylation step, the second step can be carried out at a temperature in the range about 100° C. to 500° C., preferably in the range 150° C. to 400° C, at a pressure in the range about 1.5 to 10 MPa (preferably 2 to 7 MPa) with a liquid hydrocarbon flow rate (hourly space velocity) of about 0.5 to 5 volumes per volume of catalyst per hydrogen, and with a benzene/polyalkylbenzene mole ratio of about 2:1 to 50:1.

EXAMPLE 1

The starting material was a zeolite with structure type EUO, EU-1 zeolite. as synthesised, comprising an organic template, silicon and aluminium, with a global Si/Al atomic ratio of 13.6, and a sodium content of about 1.5% with respect to the weight of dry EU-1 zeolite, corresponding to an atomic ratio Na/Al of 0.6.

This EU-1 zeolite first underwent dry calcining at 550° C. in a stream of air for 6 hours. The solid obtained then underwent three ion exchange steps in a 10 N NH4NO3 solution at about 100° C. for 4 hours per exchange step.

After these treatments, the EU-1 zeolite in its $NH_4$ form had a global Si/Al atomic ratio of 18.3, a sodium content with respect to the weight of dry EU-1 zeolite of 50 ppm by weight, corresponding to a Na/Al atomic ratio of 0.003, a specific surface area measured by the BET method of 407 $m^2/g$ and a pore volume, measured at −196° C. and at $P/P_0=0.15$, of 0.16 $cm^3$ of liquid nitrogen per gram. In the EU-1 zeolite, 100% of the aluminium atoms were in tetrahedral coordination, according to aluminium 27 NMR analysis.

The EU-1 zeolite was then formed by extrusion with an alumina gel to obtain, after drying and calcining in dry air, a support constituted by extrudates 1.4 mm in diameter which contained 60% by weight of EU-1 zeolite in its H form and 40% of alumina. The pore diameter of the prepared catalyst, measured using mercury porosimetry, was in the range 40 to 90 Å, the distribution of the diameters of these mesopores being unimodal and centred on 70 Å. The bed crush strength, obtained using the Shell method, was 1.1 MPa.

The catalyst thus prepared was used to alkylate benzene using 1-dodecene. The following operation conditions were used:

temperature: 220° C.

operating pressure: 4 MPa

HSV: 1 1/l/h benzene/1-dodecene mole ratio: 5.4 mol/mol.

Under such operating conditions, the conversion, expressed with respect to the 1-dodecene, was 53.4%. The results of selectivities for 2-, 3-, 4-, 5- and 6-phenylalkane, obtained after reaction, are shown in Table 1.

TABLE 1

| Compounds | Selectivities |
| --- | --- |
| 2-phenylalkane | 17.13 |
| 3-phenylalkane | 5.69 |
| 4-phenylalkane | 3.69 |
| 5-phenylalkane | 3.13 |
| 6-phenylalkane | 2.84 |
| Branched | 20.92 |

What is claimed is:

1. A process for producing at least one compound selected from 2-, 3-, 4-, 5- and 6-phenylalkanes by alkylating benzene in an alkylation zone using at least one olefin containing at least 9 carbon atoms per molecule, in the presence of a solid zeolitic catalyst, characterized in that the catalyst comprises a matrix and a zeolite with structure type EUO having a crystal size less than 0.2 micrometers, said zeolite comprising silicon and at least one element T selected from the group consisting of aluminum, iron, gallium and boron, with an oversall Si/T atomic ratio of more than 5; and characterized in that said alkylation is carried out at a pressure in the range 0.1 to 10 MPa, a temperature in the range of 30° C. to 400° C., with an hourly space velocity of 0.50 to 200 $h^{-1}$, and a benzene/olefin(s) mole ratio in the range of 1:1 to 50:1.

2. A process according to claim 1, in which the production of 2-, 3-, 4-, 5- and 6-phenylalkanes is simultaneous.

3. A process according to claim 1, in which the olefin is linear.

4. A process according to claim 1, in which the olefin is branched.

5. A process according to claim 1, in which the crystals are arranged in aggregates with a grain size such that the value of Dv,90 is 500 μm or less.

6. A process according to claim 1, in which the olefin contains 9 to 16 carbon atoms per molecule.

7. A process according to claim 1, in which the olefin contains 14 to 20 carbon atoms per molecule.

8. A process according to claim 1, in which the matrix is selected from the group consisting of clays, aluminas, silica, magnesia, zirconia, titanium oxide, boron oxide and combinations thereof.

9. A process according to claim 1, characterized in that the catalyst is formed into beads or extrudates.

10. A process according to claim 1, characterized in that the mechanical strength of the catalyst is such that the bed crush strength is more than 0.5 MPa.

11. A process according to claim 1, in which the zeolite with structure type EUO is EU-1 zeolite.

12. A process according to claim 1, characterized in that the element T in the catalyst is selected from the group consisting of aluminium and boron.

13. A process according to claim 1, characterized in that the matrix of the catalyst is alumina.

14. A process according to claim 1, characterized in that the zeolite of the catalyst is at least partially in its acid form with an Na/T atomic ratio of less than 0.5.

15. A process according to claim 1, characterized in that the catalyst contains 1% to 95% by weight of at least one zeolite with structure type EUO with respect to the total catalyst weight.

16. A process according to claim 1, further comprising fractionating product obtained from the alkylation zone into a first fraction comprising unconverted benzene, a second fraction comprising at least one unconverted olefin, a third fraction comprising phenylalkanes and a fourth fraction comprising at least one polyalkylbenzene, and recycling at least a portion of said fourth fraction to the alkylation zone.

17. A process according to claim 1, further comprising fractionating product obtained from the alkylation zone into a first fraction comprising unconverted benzene, a second fraction comprising at least one unconverted olefin, a third fraction comprising phenylalkanes and a fourth fraction comprising at least one polyalkylbenzene, reacting at least a portion of said fourth fraction in a transalkylation zone, different from the zone for alkylating benzene containing a catalyst with structure type EUO, said transalkylation zone containing a transalkylation catalyst and being maintained under conditions for forming monoalkylbenzene by reaction between the polyalkylbenzene(s) and benzene.

18. A process according to claim 17, in which the transalkylation zone is operated at a temperature in the range about 100° C. to 500° C., at a pressure in the range about 1.5 to 10 MPa, with a liquid hydrocarbon flow rate (space velocity) of about 0.5 to 5 volumes per volume of catalyst per hour, and with a benzene/polyalkylbenzene mole ratio of about 2:1 to 50:1.

19. A process according to claim 16, in which at least a portion of the first fraction is recycled to the alkylation zone.

20. A process according to claim 16, in which at least a portion of the second fraction is recycled to the alkylation zone.

21. A process according to claim 1, wherein the zeolite crystals are in the form of aggregates having a value of Dv,90 less than 50 micrometers.

22. A process according to claim 21, wherein the zeolite having a EUO structure is an EU-1, ZSM-50, or TPZ-3 zeolite.

* * * * *

UNITED STATES PATENT AND TRADEMARK OFFICE
CERTIFICATE OF CORRECTION

PATENT NO. : 6,429,345 B1
DATED : August 6, 2002
INVENTOR(S) : Joly et al.

It is certified that error appears in the above-identified patent and that said Letters Patent is hereby corrected as shown below:

<u>Title page,</u>
Item [54], change "PRODUCTION" to -- PRODUCING --.

Signed and Sealed this

Thirteenth Day of May, 2003

JAMES E. ROGAN
*Director of the United States Patent and Trademark Office*